US00PP26338P2

(12) United States Plant Patent
Delabroye

(10) Patent No.: US PP26,338 P2
(45) Date of Patent: Jan. 19, 2016

(54) ***HEUCHERA* PLANT NAMED 'SILVER HEART'**

(50) Latin Name: ***Heuchera* hybrid**
Varietal Denomination: Silver Heart

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 140 days.

(21) Appl. No.: 13/999,736

(22) Filed: Mar. 18, 2014

(51) Int. Cl.
*A01H 5/12* (2006.01)

(52) U.S. Cl.
USPC ..... Plt./440

(58) Field of Classification Search
USPC ..... Plt./440
See application file for complete search history.

*Primary Examiner* — June Hwu
(74) *Attorney, Agent, or Firm* — Penny J. Aguirre

(57) ABSTRACT

A new cultivar of hybrid *Heuchera* named 'Silver Heart', characterized by its uniquely colored foliage with leaves that are reddish brown with a silver overlay, its floriferous flowering habit, its purple-red flowering stems with numerous dark pink flowers, and its compact plant habit.

2 Drawing Sheets

Botanical classification: *Heuchera* hybrid.
Cultivar designation: 'Silver Heart'.

CROSSS REFERENCE TO RELATED APPLICATIONS

This application is co-pending with a U.S. Plant Patent Application filed for a plant derived from the same breeding program that is entitled *Heuchera* Plant Named 'Encore' (U.S. Plant Pat. No. 19,578) and *Heuchera* Plant Named 'Beaujolais' (U. S. Plant Pat. No. 19,577).

BACKGROUND OF THE INVENTION

The present invention relates to a new and distinct cultivar of *Heuchera* of hybrid origin, botanically known as a *Heuchera* and is hereinafter referred to by its cultivar name 'Silver Heart'.

The new cultivar arose from an ongoing breeding program by the Inventor in Hantay, France. The Inventor sowed seeds that were pooled from crosses made between proprietary plants in his breeding program in 2009. The Inventor selected 'Silver Heart' in 2011 as a single unique plant amongst the 500 seedlings that were evaluated from the above crosses. The exact parentage is unknown.

Asexual propagation of the new cultivar was first accomplished by the Inventor by leaf bud cuttings under the direction of the Inventor in June of 2013 in Paraiso, Cartago, Costa Rica. Asexual propagation of the new cultivar by leaf bud cuttings has shown that the unique features are stable and reproduced true to type in successive generations.

SUMMARY OF THE INVENTION

The following traits have been repeatedly observed and represent the characteristics of the new cultivar. These attributes in combination distinguish 'Silver Heart' as a new and unique cultivar of *Heuchera*.

1. 'Silver Heart' exhibits uniquely colored foliage with leaves that are reddish brown with a silver overlay.

2. 'Silver Heart' exhibits a floriferous flowering habit.
3. 'Silver Heart' exhibits purple-red flowering stems with numerous dark pink flowers.
4. 'Silver Heart' exhibits a compact plant habit.

'Silver Heart' can be most closely compared to the cultivars 'Encore' and 'Beaujolais' for its similarity in having foliage that is reddish in color. 'Encore' differs from 'Silver Heart' in having foliage that is less brown in color in the leaf centers and in developing more distinct veins and a greater amount of silver overlay as the leaves mature, leaf lobes that are more rounded, and in being much less floriferous. 'Beaujolais' differs from 'Silver Heart' in having leaves that are longer and wider and greyed-orange to greyed-red in color and in being much less floriferous.

BRIEF DESCRIPTION OF THE DRAWING

The accompanying colored photographs illustrate the overall appearance and distinct characteristics of the new *Heuchera*. The photographs were taken of a plant two years in age as grown outdoors in a trial bed in Hantay, France.

The photograph in FIG. 1 provides a view of the plant habit of 'Silver Heart'.

Figure 1:
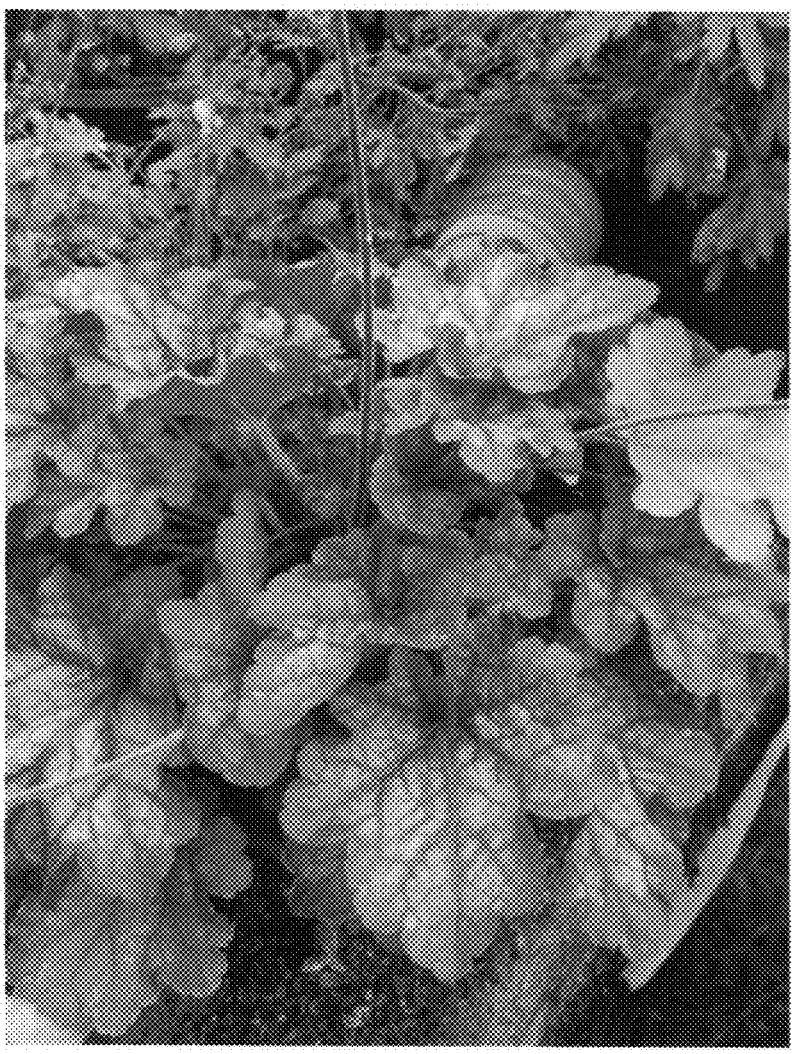
Figure 2:
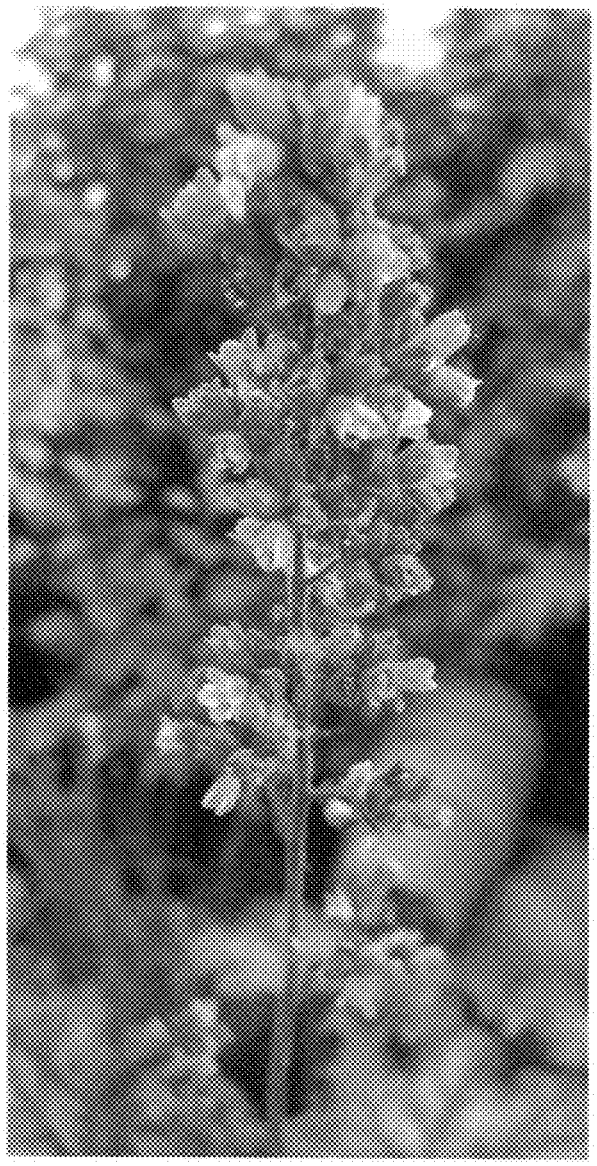

The photograph in FIG. 2 provides a close-up view of an inflorescence of 'Silver Heart'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 9-week-old plants of the new cultivar as grown in an unheated greenhouse in 7-cm square containers in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Late spring into summer in Hantay, France.

*Plant type*.—Herbaceous perennial.

*Plant habit*.—Compact and mounded.

*Height and spread*.—An average of 20 cm in height to top of foliage and 40 cm in height to top of the inflorescences, reaches about 30 cm in width.

*Hardiness*.—At least in U.S.D.A. Zones 3 to 9.

*Diseases and pests*.—No susceptibility or resistance to pests and diseases has been observed.

*Root description*.—Fibrous roots on woody rootstalks.

*Branching habit*.—Basal rosette, no lateral branches.

*Propagation*.—Leaf bud cuttings and In vitro propagation.

*Growth rate*.—Moderate.

Foliage description:

*Leaf shape*.—Broad ovate to near orbicular.

*Leaf division*.—Simple.

*Leaf base*.—Hastate, moderately overlapping.

*Leaf apex*.—Obtuse.

*Leaf venation*.—Laciniate, upper veins; 177C to 177D, lower veins; 186A.

*Leaf margins*.—Lobed with an average of 7 lobes per leaf, lobe margins are crenate.

*Leaf attachment*.—Petiolate.

*Leaf arrangement*.—Alternate, basal rosettes.

*Leaf surface*.—Upper side is matte and smooth, lower side is very slightly glossy and sparsely covered with short hairs, average length of 1.5 mm and NN 155D in color.

*Leaf color*.—Young upper surface; 178A, margins 174A to 174B, young lower surface; N186D, mature upper surface; 199A to 199B, center is between 199D and N200D, mature lower surface; 182C and 185C.

*Leaf size*.—Average of 9.4 cm in length and 7.9 cm in width.

*Leaf quantity*.—13 per basal rosette.

*Petioles*.—Average of 12.2 cm in length and 2 mm in diameter, color is 177C to 177D, base is 181A to 181B, surfaces covered with densely soft pubescence, average of 2.5 mm in length and NN155D in color.

*Stipules*.—Small leafy stipules at the base of each petiole, narrow acute apex, with an average of 1 cm in length and 4 mm in width and 181B to 181C in color, both surfaces are pubescent.

Flower description:

*Inflorescence type*.—Numerous bell-shaped flowers arranged on pyramidal panicles on flower scapes emerging from the base of the rosette.

*Inflorescence size*.—An average of 8.5 cm in height (excluding peduncle), and 2.7 cm in width.

*Flower fragrance*.—Very faint.

*Flower quantity*.—Average of 24 flowers per stem and 37 flowers per inflorescence.

*Flower lastingness*.—Average of one week, self-cleaning.

*Flower buds*.—Obovate in shape, an average of 5 mm in length and 3 mm in diameter, color; 50B.

*Flower aspect*.—Outward to slightly upright.

*Flower type*.—Campanulate.

*Flower size*.—About 8 mm in depth (height) and 8 mm in diameter.

*Petals*.—Average of 5, rotate arrangement and implanted in the hypanthium at the lower half of the calyx, petals and filaments are fused, narrow elliptic in shape, margin is entire, apex is acute, upper and lower surface is dull and smooth, color: upper and lower surface when opening and fully open; N155B, tinged 69D.

*Calyx*.—Campanulate, 8 mm in length and 8 mm in diameter.

*Sepals*.—Campanulate hypanthium, average of 5, fused into hypanthium, elliptic in shape, about 8 mm in length and 3 mm in width, margin is entire, apex is acute, fused base, color: immature upper and lower surface; N170C, base 171C to 171D, mature upper surface; N170C, base 146D, mature lower surface; N170C, base 171C to 171D.

*Peduncles*.—Average of 385 cm in length and 2 mm in diameter, moderate strength, held at a 75° angle to soil level, color of both surfaces; 181A, fading to 177C to 177D, very densely covered with soft pubescence, average length of pubescence is 2.5 mm and NN155D in color.

*Pedicels*.—Average of 2 mm in length and 0.5 mm in width, moderate strength, color is 53B.

Reproductive organs:

*Gynoecium*.—2 pistils, 3.5 mm in length, stigma is pointed in shape and N170C to N170D in color, styles are about 3.5 mm in length and 150D in color, ovaries are 145C in color.

*Androcoecium*.—5 stamens, anthers are ovate in shape, about 0.5 mm and 26A in color, filament 3 mm in length and N155B in color, pollen is low in quantity and 28A to 28B in color.

*Seed/fruit*.—No fruit or seeds detected to date.

It is claimed:

1. A new and distinct cultivar of hybrid *Heuchera* plant named 'Silver Heart' as herein illustrated and described.

* * * * *